US010182778B2

(12) United States Patent
Jang et al.

(10) Patent No.: US 10,182,778 B2
(45) Date of Patent: Jan. 22, 2019

(54) SWITCH DEVICE, AND X-RAY IMAGING APPARATUS AND ELECTRONIC APPARATUS INCLUDING THE SAME

(71) Applicant: SAMSUNG ELECTRONICS CO., LTD., Suwon-si (KR)

(72) Inventors: Ku-Il Jang, Yongin-si (KR); Chang Jin Yang, Seoul (KR); Hyun Joong Chae, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 203 days.

(21) Appl. No.: 15/060,813

(22) Filed: Mar. 4, 2016

(65) Prior Publication Data
US 2016/0256124 A1 Sep. 8, 2016

(30) Foreign Application Priority Data
Mar. 4, 2015 (KR) .................. 10-2015-0030541

(51) Int. Cl.
*A61B 6/00* (2006.01)
*F16M 11/04* (2006.01)

(52) U.S. Cl.
CPC ............ *A61B 6/4452* (2013.01); *A61B 6/467* (2013.01); *A61B 6/54* (2013.01); *A61B 6/547* (2013.01); *F16M 11/046* (2013.01); *A61B 6/4233* (2013.01); *A61B 6/4464* (2013.01); *A61B 6/4476* (2013.01); *A61B 6/587* (2013.01)

(58) Field of Classification Search
CPC ......... A61B 6/4452; A61B 6/54; A61B 6/467; A61B 6/547; A61B 6/4233; A61B 6/4464; A61B 6/4476; A61B 6/587; A61B 6/588; F16M 11/046
See application file for complete search history.

(56) References Cited

U.S. PATENT DOCUMENTS

2008/0063249 A1 3/2008 Ohtsuka
2012/0082295 A1* 4/2012 Agano .................. A61B 6/405
378/62
2012/0207274 A1* 8/2012 Yang .................... A61B 6/4233
378/62

FOREIGN PATENT DOCUMENTS

| JP | H 5-43443 U | 6/1993 |
| JP | 2000149717 A | 5/2000 |
| KR | 1020090059180 A | 6/2009 |
| KR | 1020110107489 A | 10/2011 |
| KR | 1020140109721 A | 9/2014 |
| KR | 1020140121506 A | 10/2014 |
| KR | 1020140132897 A | 11/2014 |

OTHER PUBLICATIONS

Communication dated Dec. 8, 2017, issued by the European Patent Office in counterpart European application No. 16 158 403.2.
(Continued)

*Primary Examiner* — Courtney Thomas
(74) *Attorney, Agent, or Firm* — Sughrue Mion, PLLC

(57) ABSTRACT

An X-ray imaging apparatus includes an X-ray generator configured to generate X-rays; a detector configured to detect X-rays that have penetrated an object; a stand on which the detector is mounted; and a control panel mounted on the stand, and configured to operate the detector to rotate or move up or down along an extension direction of the stand.

12 Claims, 13 Drawing Sheets

(56) References Cited

OTHER PUBLICATIONS

Anonymous, "Digital Radiography: GC85A", Samsung Electronics Co., Ltd., Feb. 1, 2015, 8 pages total, XP 055286167, www.lacmedical.com/wp-content/uploads/HME_DR_GC85A_Catalog_v1.0-01.pdf.
Anonymous, "Samsung Smart Digital Radiography: GC85A", Samsung Electronics Co., Ltd., Jan. 1, 2014, 14 pages total, XP 055286173, www.raymed.com/uploads/media/GC85A-Datasheet.pdf.
Anonymous, "Create a premium DR room like no other", Jul. 1, 2014, Koninklijke Philips N.V., 46 pages total, XP 055286181, www.usa.philips.com/healthcare/product/HC712220/digitaldiagnost-digital-radiography-solutions.
Anonymous, "Digital Radiographic System with Auto-Tracking", Nov. 1, 2012, Control-X Medical, Ltd., 4 pages total, XP 055286198, www.valsoe.com/wp-content/uploads/Perform-X-DIGI-AT-HU.pdf.
Communication dated Jul. 18, 2016, issued by the European Patent Office in counterpart European Patent Application No. 16158403.2.
Communication dated Oct. 24, 2016 issued by European Patent Office in counterpart European Application No. 16158403.2.
Communication dated May 2, 2018, issued by the European Patent Office in counterpart European Patent Application No. 16158403.2.

* cited by examiner

SWITCH DEVICE, AND X-RAY IMAGING APPARATUS AND ELECTRONIC APPARATUS INCLUDING THE SAME

CROSS-REFERENCE TO RELATED APPLICATION

This application claims priority from Korean Patent Application No. 10-2015-0030541, filed on Mar. 4, 2015, the disclosure of which is incorporated herein by reference in its entirety.

BACKGROUND

1. Field

Exemplary embodiments relate to an easily operable switch device and an X-ray imaging apparatus and an electronic apparatus including the switch device.

2. Related Art

An input unit to operate various functions may be provided in electronic devices. The input unit may include various input means including a button, a track ball, a touch pad, a toggle switch, a joy stick, etc.

When a button is pressed to perform various operations of the electronic device, because any one of a plurality of buttons arranged in the input unit is pressed, an operation radius of a key may be small, and there is a high probability of an incorrect input operation. In case of the track ball, because it does not have a constant directionality, there may be an advantage in precisely controlling a movement, but there is also a disadvantage in controlling a simple movement.

The toggle switch represents a switch device which may become any one of an on state and an off state. The joy stick is a lever-type switch device having degrees of freedom in at least two directions. In the case of the joy stick, an electronic apparatus may be operated to identify movement information by a lever moved in an up and down direction, a left and right direction, or a diagonal direction.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide a switch device in which an operation unit is installed in a bracket including a double-injection-molded elastic material so that a switch is easily operable by an operation unit as well as an X-ray imaging apparatus and an electronic apparatus including the switch device.

According to an aspect of an exemplary embodiment, a switch device configured to generate a signal related to a control of an electronic apparatus includes a switch configured to be tilted on a printed circuit board, an operation unit connected to the switch, a bracket in which the operation unit is installed to be rotatable, and a support member formed of an elastic material included in the bracket to support one side of the operation unit.

The support member may be formed by a double injection molding with the bracket.

The support member may have a dome shape.

The switch device may include a safe positioning member which is positioned safely in the support member and protruded from one end of the operation unit.

When an external force is applied to the operation unit, the support member may be pressurized by the operation unit and a shape thereof may be changed.

When the external force applied to the operation unit is removed, a shape of the support member may restore to a shape before being changed.

When the external force applied to the operation unit is removed, the support member may restore to a position before applying the external force due to an elasticity of the support member.

A hole through which the switch passes may be formed on a bottom portion of the bracket.

The operation unit may be coupled to the switch passing through the hole and protruded from the bottom portion of the bracket and may operate with the switch together.

When an external force is applied to the operation unit, the switch may be tilted, and a signal related to a specific operation of the electronic apparatus may be input.

The operation unit may include an accommodating member which accommodates the switch.

The operation unit may include a protruded fixed portion in which the accommodating member is formed.

A fixing rib configured to fix the switch may be provided on an inside surface of the fixed portion in which the accommodating member is formed.

A rotation axis protruding from a side direction of the operation unit is provided.

The bracket may include an insertion hole in which the rotation axis is inserted to be rotatable.

According to another embodiment of the present invention, a switch device includes a printing circuit board including a switch which inputs an operation signal of an electronic apparatus, an operation unit configured to operate together with the switch by an external force, and a bracket fixed on the printing circuit board and in which the operation unit is installed to be rotatable. The bracket includes a support member formed of an elastic material as one body with the bracket so that the support member is pressurized by the operation unit.

When an external force is applied to the operation unit such that the operation unit rotates on a rotation axis, the operation unit and the switch may be tilted together as one body.

When the operation unit rotates about the rotation axis, the support member may be pressurized, and a shape thereof may be changed by the operation unit.

When the external force applied to the operation unit is removed, the support member may restore to a shape before applying the external force.

When a shape of the support member restores, the support member may restore to a position before applying the external force.

The support member may be formed by a double injection molding with the bracket.

A protruded rotation axis is provided in a side direction of the operation unit, and an insertion hole is provided on a side surface of the bracket into which the rotation axis is inserted to be rotatable.

The support member may be located in a direction where the switch is tilted around the switch.

BRIEF DESCRIPTION OF THE DRAWINGS

The above and/or other aspects will become more apparent by describing certain exemplary embodiments with reference to the accompanying drawings, in which.

DETAILED DESCRIPTION OF EXEMPLARY EMBODIMENTS

Figure 1:
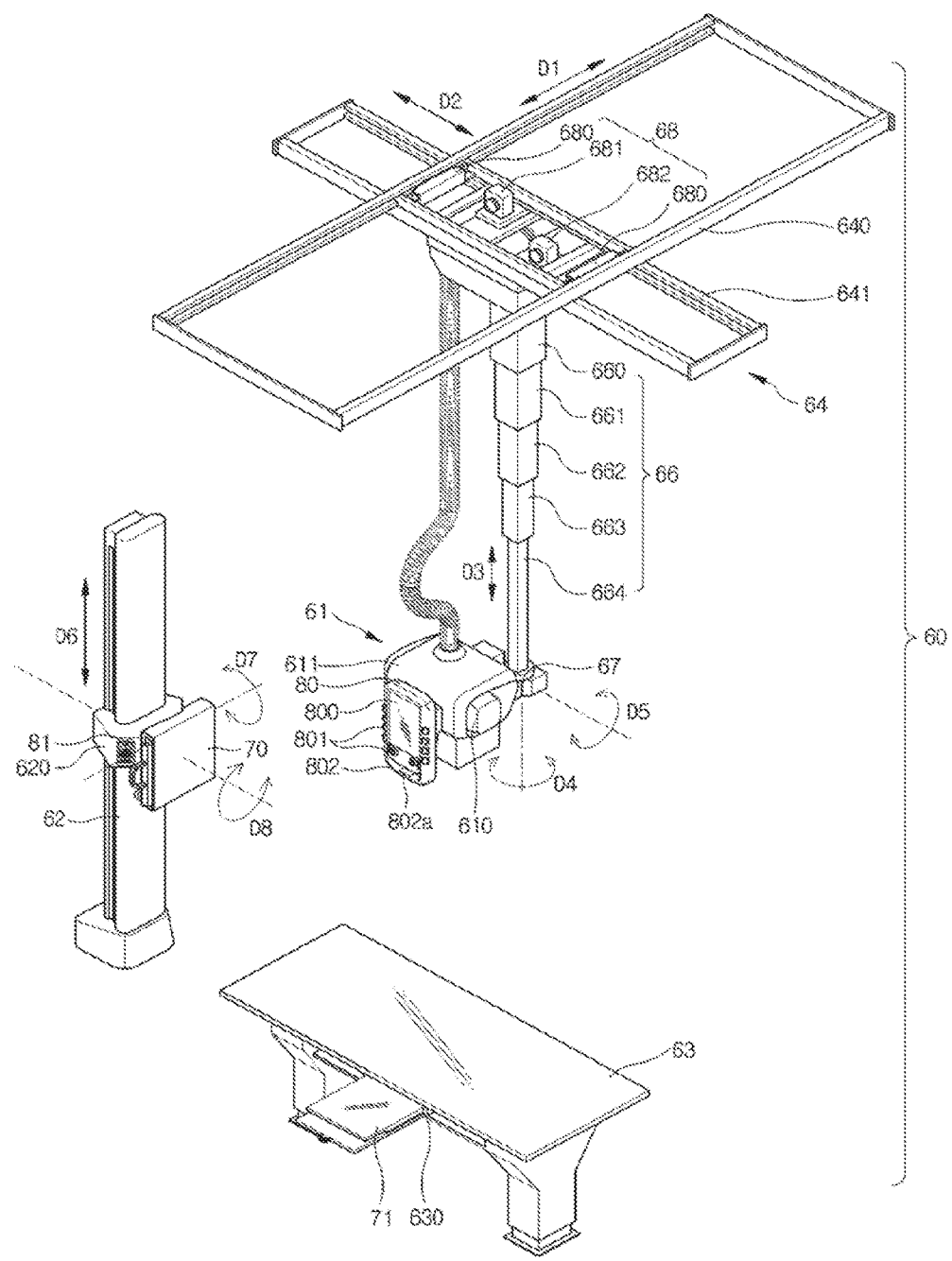
FIG. 1 is a diagram illustrating an X-ray imaging apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

FIG. 1 is a diagram illustrating an X-ray imaging apparatus according to an exemplary embodiment.

Referring to FIG. 1, an X-ray imaging apparatus 60 according to an exemplary embodiment may include an X-ray generator 61 and a detector 70 or 71. The detector 70 or 71 may be mounted on a stand 62 or installed on a table 63.

The X-ray generator 61 generates X-rays and irradiates an object. The X-ray generator 61 receives a power supply from a power supply source (not shown) to generate the X-rays. Energy of the X-rays may be controlled by a tube voltage, and an intensity of the X-ray or a dose of the X-ray may be controlled by a tube current and an exposure time of the X-ray.

The detector 70 or 71 detects X-rays penetrating an object. The detector 70 or 71 may convert the detected X-rays into electrical signals to obtain X-ray data.

The X-ray imaging apparatus 60 may include a movement apparatus 64 which moves the X-ray generator 61. The movement apparatus 64 may include guide rails 640 and 641, a moving carriage 65, and a column 66.

The guide rails 640 and 641 may include a first guide rail 640 and a second guide rail 641. The first guide rail 640 and the second guide rail 641 may be installed with a predetermined angle therebetween. For example, the first guide rail 640 and the second guide rail 641 may be installed to be perpendicular to each other. When an extending direction of the first guide rail 640 is a first direction D1 and an extending direction of the second guide rail 641 is a second direction D2, the first direction D1 and the second direction D2 may be perpendicular to each other.

The first guide rail 640 may be installed at a ceiling of an inspection room in which the X-ray imaging apparatus 60 is arranged. The second guide rail 641 may be installed under the first guide rail 640. The second guide rail 641 may be installed so that the second guide rail 641 is able to slide along the first guide rail 640. For example, rollers movable along the first guide rail 640 may be installed in the first guide rail 640, and the second guide rail 641 may be connected to the rollers and move along the first guide rail 640.

The moving carriage 65 may be arranged under the second guide rail 641. The moving carriage 65 may be arranged to be movable along the second guide rail 641. Rollers movable along the second guide rail 641 may be installed in the moving carriage 65. The moving carriage 65 may move in the first direction D1 with the second guide rail 641 and move in the second direction D2 along the second guide rail 641.

The column 66 may be located under the moving carriage 65. The column 66 may include a plurality of columns 660, 661, 662, 663, and 664. The plurality of columns 660 to 664 may be provided to be folded. The column 66 may increase or decrease in length in a third direction D3 which is an up and down direction of the inspection room in a state in which the column 66 is fixed to the moving carriage 65.

The X-ray generator 61 is a device which irradiates an object with X-rays. The X-ray generator 61 may include an X-ray source 610 and a collimator 611. The X-ray source 610 generates X-rays. The collimator 611 guides the X-rays generated by the X-ray source 610 to the object.

A rotation joint 67 may be arranged between the X-ray generator 61 and the column 66. The rotation joint 67 may couple the X-ray generator 61 to the column 66 and support a load applied to the X-ray generator 61.

The X-ray generator 61 may rotate about the rotation joint 67. The X-ray generator 61 may rotate in a fourth direction D4 or a fifth direction D5 by virtue of the rotation joint 67. The fourth direction D4 may be a direction rotating about an axis parallel with the third direction D3. Further, the X-ray generator 61 may be connected to the column 66 by the rotation joint 67 and may move linearly in the first direction D1, the second direction D2, or the third direction D3.

A driver 68 may be provided to move the X-ray generator 61 in the first direction D1 to the fifth direction D5. The driver 68 may be an electrically driven motor.

The driver 68 may be provided to correspond to the first direction D1 to the fifth direction D5. For example, the driver 68 may include a first driver 680 which moves the second guide rail 641 in the first direction D1 and second drivers 681 and 682 which move the moving carriage 65 in the second direction D2. The first driver 680 may be arranged near the first guide rail 640, and the second drivers 681 and 682 may be arranged near the second guide rail 641.

The driver 68 may include a third driver (not shown) which increases or decreases a length of the column 66 in the third direction D3, a fourth driver (not shown) which rotates the X-ray generator 61 in the fourth direction D4, and a fifth driver (not shown) which performs rotational movement on the X-ray generator 61 in the fifth direction D5. The third driver may be arranged inside the moving carriage 65. The fourth driver and the fifth driver may be arranged near the rotation joint 67.

The X-ray imaging apparatus 60 may further include a stand 62 on which the detector 70 and 71 is mounted or a table 63 on which the detector 71 is installed. When an object located on the table 63 is imaged, the detector 71 may be inserted in an accommodating member 630 provided in the table 63.

The detector 70 may be mounted on the stand 62 according to an object to be imaged. For example, when imaging a standing object, the detector 70 may be mounted on the stand 62. The detector 70 mounted on the stand 62 may be provided to move up or down along an extension direction of the stand 62.

The detector 70 may be mounted on the stand 62 via an arm 620 mounted to move up or down along the extension direction of the stand 62. The extension direction of the stand 62 may be referred to as a sixth direction D6.

Figure 2A:
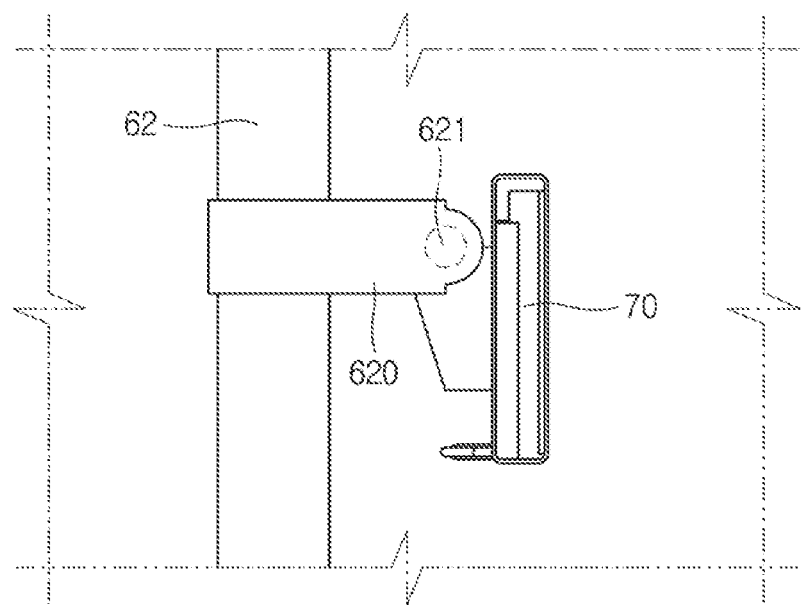
FIGS. 2A, 2B, 2C, and 2D are side views illustrating detectors according to an exemplary embodiment.
Figure 2B:
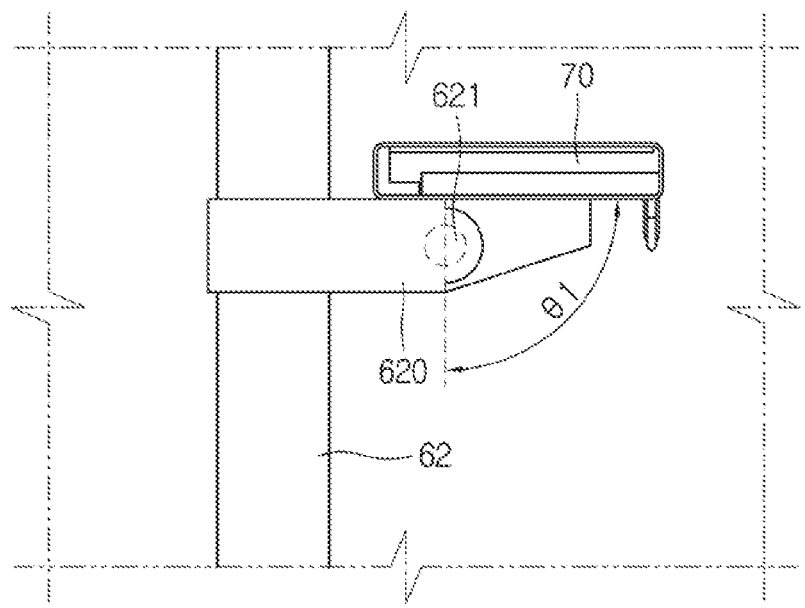
Figure 2C:
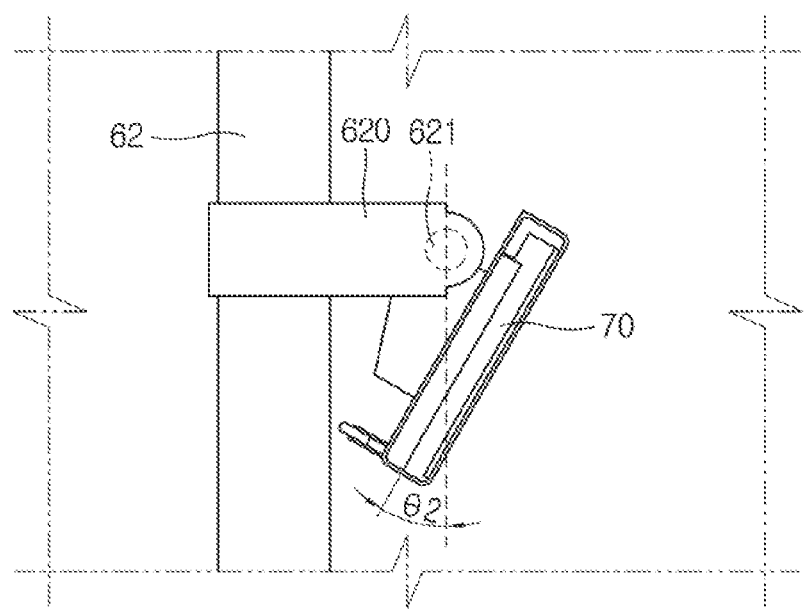

The detector 70 may be mounted on the arm 620 so that the detector 70 rotates on a rotation axis 621 (refer to FIGS. 2A to 2C). A direction in which the detector 70 rotates on the rotation axis 621 may be referred to as a seventh direction D7.

Figure 2D:
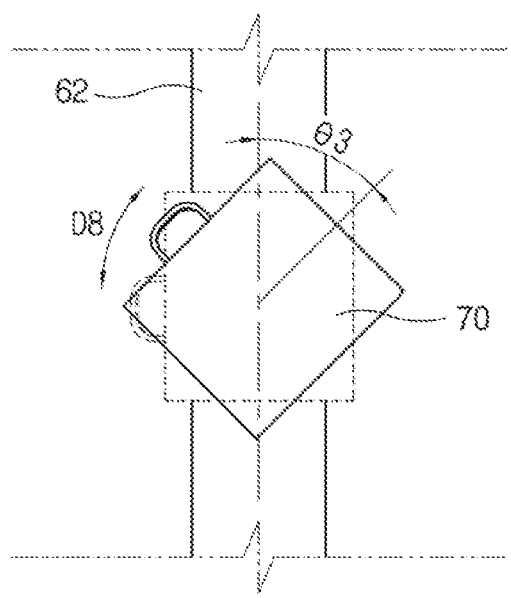

A direction of a straight line perpendicular to a surface of the detector 70 about which the detector 70 rotates may be referred to as an eighth direction D8 (refer to FIG. 2D). The detector 70 may be rotated in the eighth direction D8 according to the posture of an object to be imaged with the X-rays. The rotation of the detector 70 in the eighth direction D8 may be accomplished manually or automatically.

An input unit 80 into which various kinds of information on X-ray imaging is input and which operates each device may be disposed on one side surface of the X-ray generator 61. A control of an operation of the X-ray generator 61 may be performed by an operation of the input unit 80. Further, the movement of the X-ray generator 61 and the like may be performed by the input unit 80.

The input unit 80 may include a display 800 including interfaces for inputting various kinds of information on X-ray imaging or operating devices as well as a handle 802 onto which an operator holds. Further, a button 801 for operating an X-ray imaging apparatus may be included. Means for operating the X-ray imaging apparatus is not limited by a form of the button 801. Hereinafter, the case that the button 801 provided in the input unit 80 is operated for operating the X-ray imaging apparatus will be described.

When an object is imaged using the X-ray imaging apparatus, the display 800 of the input unit 80 may provide a preview function which displays an X-ray image so that an operator can immediately thereafter examine the image. By displaying the image on the display 800, the operator may immediately examine the image at the workstation and also at the operation unit.

The display 800 includes a touch screen with which a touch gesture of the operator may be input. Soft-key type buttons which perform the same function as the physical buttons 801 for operating devices may be implemented on the touch screen. The operator may input the same commands as the commands when the physical buttons are operated by touching buttons implemented on the touch screen.

The handle 802 may be provided on one side of the input unit 80. Though the handle 802 is at a bottom portion of the input unit 80 in FIG. 1, the position of the handle 802 is not limited to that shown in FIG. 1.

The operator may move the X-ray generator 61 by holding the handle 802 of the input unit 80 and applying a force. This may be referred to as the manual movement mode. The X-ray generator 61 being moved by buttons 801 provided in the input unit 80 may be referred to as the automatic movement mode.

A mode change unit 802a may be provided in the handle 802. Operating the mode change unit 802a may switch between the automatic movement mode and the manual movement mode. The mode change unit 802a may be provided on the handle 802 of the input unit 80 in the form of a button or a switch. For example, the mode change unit 802a may be provided in the form of a switch that is pressurized when the handle 802 is held. When the operator pressurizes the mode change unit 802a by holding the handle 802, the mode of the X-ray generator 61 may be switched to the manual movement mode, and when the operator releases the pressure on the mode change unit 802a by releasing the handle 802, the mode of the X-ray generator 61 may become the automatic movement mode. The operator may move the X-ray generator 61 toward a desired direction while the mode change unit 802a provided in the handle 802 is pressurized.

The X-ray generator 61 may include a measurement unit to measure a force or a torque applied by the operator so that the X-ray generator 61 comprehends an operator's intention of movement. The measurement unit may include a force sensor or a torque sensor. Information on a magnitude and a direction of the force or the torque measured by the measurement unit may be transmitted to a control unit (not shown) and the control unit may operate a motor in response to the magnitude of the force or the torque so that the X-ray generator 61 easily moves toward a direction which the operator desires.

The operator may operate the input unit 80 so that the X-ray generator 61 moves toward the stand 62 or toward the table 63. The input unit 80 may include an operation means for controlling a position of the detector 70 mounted on the stand 62.

A control of an arrangement of the detector 70 mounted on the stand 62 or a movement of the X-ray generator 61 may be accomplished by the control panel 81. The control panel 81 may be fixed to one side surface of the stand 62. The control panel 81 may be provided in the form of a remote control separate from the stand 62 so that remote controlling is possible. Hereinafter, an embodiment in which the control panel 81 is fixed to one side surface of the stand 62 will be described.

The operator may control a movement of the X-ray generator 61 or an arrangement of the detector 70 mounted on the stand 62 using the control panel 81 at a position separate from the X-ray imaging apparatus 60.

The X-ray generator 61 may include a sensor (not shown) detecting a position of the detector 70. The X-ray generator 61 may move to a position at which an imaging according to the position of the detector 70 is possible using information detected by the sensor.

Therefore, the operator may move the X-ray generator 61 to a position at which imaging an object is possible according to an arrangement of the detector 70 only by controlling the detector 70 mounted on the stand 62 via the input unit 80 or the control panel 81 without having to control the position of the X-ray generator 61. The X-ray generator 61 may also be controlled to move independently regardless of the position of the detector 70.

FIGS. 2A, 2B, 2C, and 2D are side views illustrating detectors according to an exemplary embodiment.

Referring to FIGS. 2A to 2C, the detector 70 may rotate about the rotation axis 621 with an appropriate angle according to the position of an object to be imaged by the X-rays.

When a front surface of a standing object is to be imaged, the detector 70 may be arranged parallel to the stand 62 as shown in FIG. 2A. The detector 70 may rotate about the rotation axis 621 clockwise or counterclockwise according to the position of an object.

For example, the detector 70 may rotate counterclockwise by 90° (θ1). The detector 70 may rotate about the rotation axis 621 clockwise. For example, the detector 70 may rotate clockwise by 20° (θ2). The angle with which the detector 70 rotates about the rotation axis 621 clockwise or counterclockwise is not limited to those described above.

Referring to FIG. 2D, the detector 70 may rotate in an eighth direction D8 according to the position of an object to be imaged by X-rays. The detector 70 may rotate in the eighth direction D8 with a predetermined angle θ3. For example, an angle (θ3) with which the detector 70 rotates in the eighth direction D8 may be 0° to 90°. The detector 70 may be fixed at each of the positions having rotated angles of 0°, 45°, and 90° in the eighth direction D8.

The rotation of the detector 70 in the eighth direction D8 may be accomplished manually without an operation of a motor or automatically by virtue of an operation of the motor which is operated by controlling the input unit 80 or the control panel 81.

The detector 70 may move up or down in a sixth direction D6 which is an extension direction of the stand 62 according to the position of an object.

The operation where the detector 70 moves up or down in the sixth direction D6 and the detector 70 rotates around the rotation axis 621 may be accomplished by controlling the input unit 80 or the control panel 81. When the detector 70 moves up or down or rotates by controlling the input unit 80 or the control panel 81, the X-ray generator 61 may move to a position at which imaging an object in tandem with the movement of the detector 70 is possible.

Hereinafter, a structure of the control panel 81 which is able to control an operation of the detector 70 will be described. The input unit 80 may similarly include at least a part of the structure of the control panel 81.

The control panel 81 may be fixed to the stand 62. The control panel 81 is prevented from being lost by being fixed at the stand 62.

The control panel 81 may be provided in the form of a remote control separate from the stand 62 so that remote controlling is possible. When the control panel 81 has the form of the remote control, the control panel 81 may further include a sensor which may transmit signal to and receive signal from the detector 70.

Figure 3A:
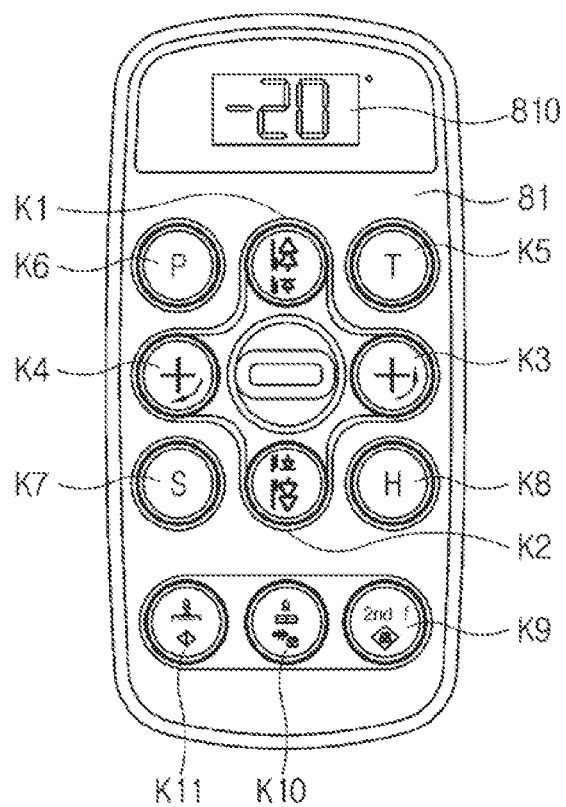
FIGS. 3A and 3B are perspective views illustrating control panels according to an exemplary embodiment.
Figure 3B:
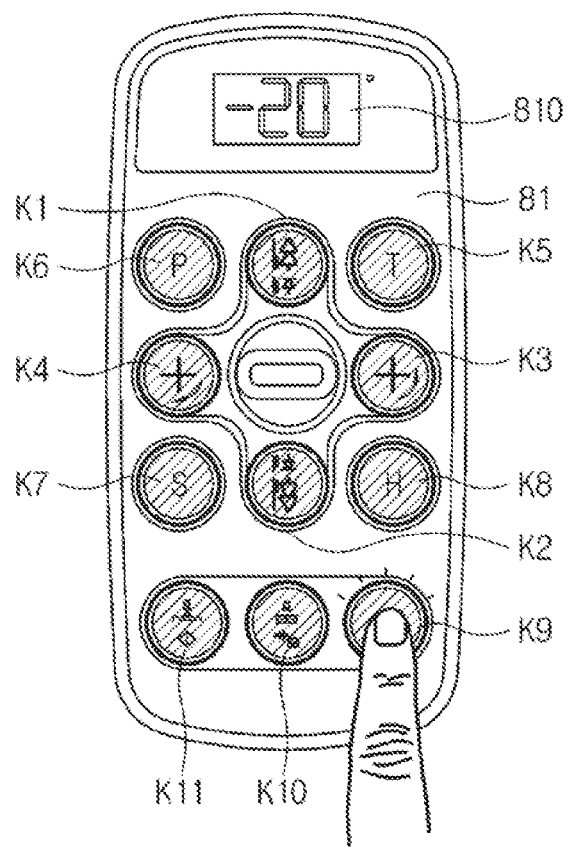

FIGS. 3A and 3B are perspective views illustrating control panels according to an exemplary embodiment.

Referring to FIGS. 3A and 3B, the control panel 81 may include a display 810 and a plurality of buttons K1 to K11. Further, the control panel 81 may include a switch device 1 which is able to control a position of the detector 70 (refer to FIG. 4).

Rotation angle and the like of the detector 70 may be displayed on the display 810. For example, as shown in FIG. 2A, the position at which the detector 70 is arranged parallel to an extension direction of the stand 62 may be displayed as 0°. As shown in FIG. 2B, the position at which the detector 70 rotates counterclockwise and arrives to be perpendicular to the extension direction of the stand 62 may be displayed as 90°. When the detector 70 rotates clockwise by 20° from a reference position at which the detector 70 is arranged parallel to the extension direction of the stand 62, −20° may be displayed on the display 810.

The operation of the detector 70 may be controlled by controlling a plurality of buttons K1 to K11 provided in the input unit 80.

When the entire plurality of buttons for controlling various operations of the detector 70 are disposed in the input unit 80, situations occur where the size of the input unit 80 becomes excessively large or the separation distance between buttons decreases such that incorrect buttons are pressed.

Therefore, at least one of a plurality of buttons may be provided to control two or more operations so that an optimal separation distance between buttons may be obtained and the size of the input unit 80 is prevented from being excessively large. A button that is set to control two or more operations may control one of the predetermined operations by turning the shift button K9 on or off.

Hereinafter, a button that is set to control two or more operations may be referred to as a function key.

When the shift button K9 is in an on-state, the shift button K9 may be brightly displayed by a light source located behind the shift button K9. To display whether the shift button K9 is in the on-state is also possible by other means. Further, a separate display lamp may be provided on one side of the shift button K9. When the shift button K9 is in the on-state, the display lamp may be provided to become the on-state, and when the shift button K9 is in the off-state, the display lamp may be provided to become the off-state.

When the shift button K9 is in the on-state, the plurality of buttons K1 to K8, K10, and K11 provided in the control panel 81 may be in the on-state and may be brightly displayed by a light source located behind. When the shift button K9 is in the on-state, the plurality of buttons K1 to K8, K10, and K11 provided in the control panel 81 may be in the operable state.

When the shift button K9 is in an off-state, the display lamp illuminating the shift button K9 and a function key may become the off-state. When the shift button K9 is in the off-state, the plurality of buttons K1 to K8, K10, and K11 provided in the control panel 81 may be in a locked state so that, even when pressure is applied, the buttons become a state where operation of the detector 70 or the X-ray generator 61 cannot be performed. The function to display the on or off state of the shift button K9 is not limited to the on or off state of a display lamp but may be realized by various methods.

When the shift button K9 is pressed for a long time, e.g., 3 seconds or more, all the buttons provided in the input unit 80 including the shift button K9 may enter a locked state. In the locked state, even when buttons provided in the input unit 80 are pressed, the detector 70 or the X-ray generator 61, etc. may not operate. In the locked state, all the light sources displaying the on/off states of the buttons in the control panel 81 may be turned off. In the locked state, when the shift button K9 is pressed again for a long time, e.g., 3 seconds or more, the locked state may be released.

In the off-state of the shift button K9, when the first button K1 is pressed, the detector 70 may move up to a specified position based on predetermined information. In the on-state of the shift button K9, when the first button K1 is pressed, the detector 70 may move up with high speed along the extension direction D6 of the stand 62. Here, the detector 70 may move up with high speed when the first button K1 is pressed, and the movement may be stopped when the pressure on the first button K1 is released.

In the off-state of the shift button K9, when the second button K2 is pressed, the detector 70 may move down to a specified position based on predetermined information in the second button K2. In the on-state of the shift button K9, when the second button K2 is pressed, the detector 70 may move down with high speed along the extension direction D6 of the stand 62. Here, the detector 70 may move down with high speed when the second button K2 is pressed, and the movement may be stopped when the pressure on the second button K2 is released.

In the off-state of the shift button K9, when the third button K3 or the fourth button K4 is pressed, the detector 70 may rotate about the rotation axis 621 by a specified angle based on predetermined information in the third button K3 or the fourth button K4. In the on-state of the shift button K9, when the third button K3 is pressed, the detector 70 may further rotate about the rotation axis 621 counterclockwise. In the on-state of the shift button K9, when the fourth button K4 is pressed, the detector 70 may further rotate about the rotation axis 621 clockwise.

In the on-state of the shift button K9, after one of the first button K1 to the fourth button K4 is controlled, the shift button K9 may be automatically turned off.

The fifth button K5 to the eighth button K8 may control one operation regardless of the on or off state of the shift button K9.

The fifth button K5 and the seventh button K7 may control the X-ray generator 61. When the fifth button K5 is pressed, the X-ray generator 61 may move to the detector 70 provided in the stand 62. When the seventh button K7 is pressed, the X-ray generator 61 may move to the table 63 so that X-ray imaging is accomplished on the table 63.

When the sixth button K6 is pressed, the detector 70 may move to a predetermined initial standby position. The predetermined initial standby position may be predetermined according to a user environment. For example, the X-ray generator 61 may move toward a ceiling of an inspection room, and the detector 70 may be arranged so that one surface of the detector 70 is positioned parallel to an extension direction of the stand 61.

When the eighth button K8 is pressed, as shown in FIG. 2A, the detector 70 may be positioned perpendicular to the extension direction of the stand 62. The detector 70 may be parallel with a bottom surface, and X-ray imaging may be performed with an object placed on the detector 70. Here, 90° may be displayed on the display 81.

The fifth button K5 to the eighth button K8 may perform one function regardless of the on or off state of the shift button K9. The fifth button K5 to the eighth button K8 may be pressed and perform a specified function when the shift button K9 is in the on-state. In the on-state of the shift button K9, after one of the fifth button K5 to the eighth button K8 is controlled, the shift button K9 may be turned off. The shift button K9 needs to be pressed and in the on-state so that the fifth button K5 to the eighth button K8 perform specified functions.

As described above, the fifth button K5 to the eighth button K8 perform specified functions only when the shift button K9 is pressed, and therefore accidents due to the fifth button K5 to the eighth button K8 and the like provided in the control panel 81 being unintentionally pressed and performing the specified functions may be prevented.

The tenth button K10 and the eleventh button K11 may control operations related to an X-ray imaging mode. For example, the tenth button K10 or the eleventh button K11 may control operations such as a collimator size adjustment related to the size of an X-ray image, or an automation synchronization, etc. The tenth button K10 or the eleventh button K11 may also include a function key which may control two or more operations by the on or off operation of the shift button K9.

An arrangement of the detector 70 provided in the stand 62 may be controlled by the first button K1 to the fourth button K4 as well as the eighth button K8. Because the condition of an object to be X-ray- imaged may be different every time imaging is performed, it is required for the detector 70 to move to a predetermined position according to the buttons provided in the control panel 81 and then precisely move according to the environments of the object so that X-ray imaging on the object is easily accomplished. However, when the detector 70 is moved by the controlling of the buttons, it is hard to precisely control the position of the detector 70 due to a base speed at which the detector 70 moves.

Therefore, a switch device 1 may be provided in the input unit 80 so that the operator can approach an object and precisely control the detector 70 so that the X-ray imaging on the object is easily performed. The switch device 1 may be provided to control a position of the detector 70 by pressing an operation unit 30 provided in the input unit 80 in an up, down, left, or right direction.

When the operator presses the operation unit 30 of the switch device 1 in one direction, the detector 70 may move in the pressed direction. The detector 70 may move only while the operation unit 30 is pressed, and when the pressure of the operation unit 30 is released, the movement of the detector 70 may be stopped.

When the operation unit 30 is pressed upward, the detector 70 may move upward, and when the operation unit 30 is pressed downward, the detector 70 may move downward. The operator may precisely move the detector 70 upward or downward with a small magnitude of force required to operate the operation unit 30.

When the shift button K9 is pressed for a long time, e.g., 3 seconds or more, so that the control panel 81 is in a locked state, the switch device 1 may be in a locked state and the detector 70 may not be moved by pressurizing the switch device 1.

Hereinafter, the structure of the switch device 1 capable of controlling the operation of the detector 70 will be described.

Figure 4:
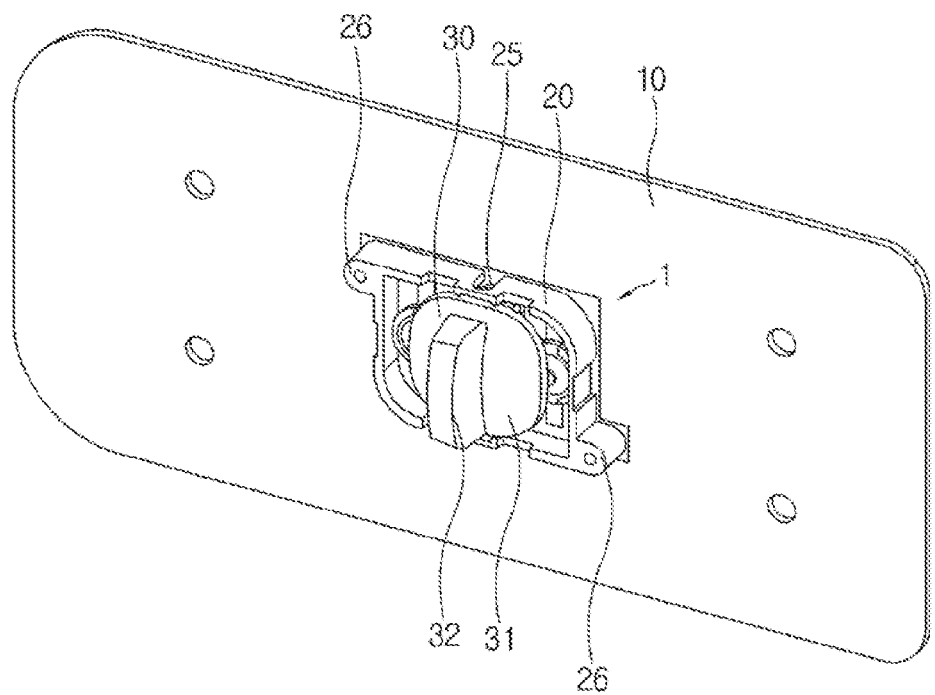
FIG. 4 is a perspective view illustrating a switch device according to an exemplary embodiment.
Figure 5:
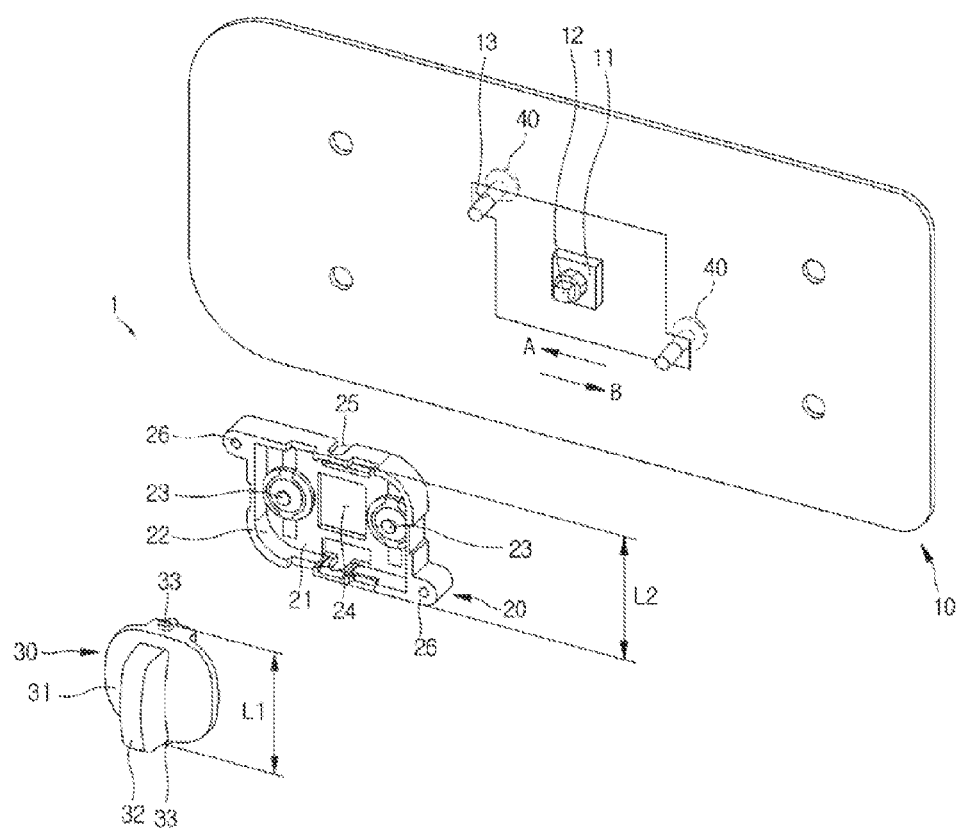
FIG. 5 is an exploded perspective view illustrating the switch device according to an exemplary embodiment.
Figure 6:
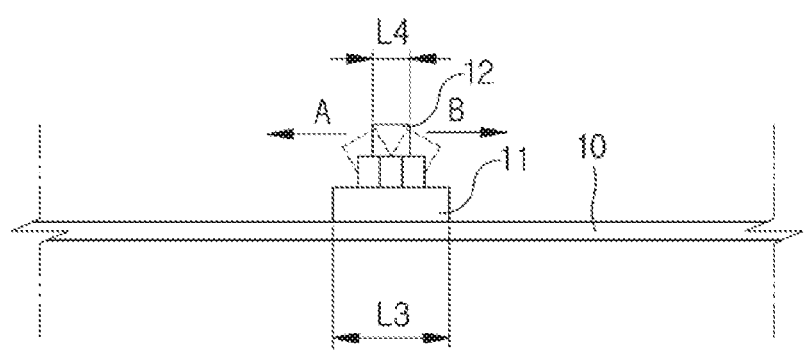
FIG. 6 is a diagram illustrating an operation of a switch according to an exemplary embodiment.

FIG. 4 is a perspective view illustrating a switch device according to an exemplary embodiment, FIG. 5 is an exploded perspective view illustrating a switch device according to an exemplary embodiment, and FIG. 6 is a diagram illustrating an operation of a switch according to an exemplary embodiment.

Referring to FIGS. 4 to 6, the switch device 1 according to an exemplary embodiment may include a switch 12, an operation unit (knob) 30 operating the switch 12, and a bracket 20 in which the operation unit 30 is installed. The switch 12 may be provided on a printed circuit board 10 included in an electronic apparatus. The printed circuit board 10 may be provided in electronic products including medical appliances, home appliances, etc. The switch 12 may be provided so that an operation of the electronic apparatus is controlled by a user's control.

The switch 12 may have a form of a lever whose one end is mounted on a pedestal 11. A diameter of L3 of the pedestal 11 may be greater than a diameter L4 of the switch 12.

The other end of the switch 12 may move in up and down directions or left and right directions by an external pressure. The other end of the switch 12 may have degrees of freedom in at least two directions. Directions in which the other end of the switch 12 moves by an external force and the degree of freedom of the switch 12 are not limited to those described above. The state where an external force is not applied to the switch 12 and the other end of the switch 12 does not move in a specified direction may be referred to as a neutral state. In the neutral state, the switch 12 may be vertically extended from one surface of the pedestal 11.

Hereinafter, an embodiment in which the other end of the switch 12 moves in a first direction A and in a second direction B opposite to the first direction A will be described. The operation control which is input may be different for the case where the switch 12 is operated in the first direction A and the case where the switch 12 is operated in the second direction B.

The bracket 20 may be mounted on the printed circuit board 10 on which the switch 12 is provided. Through holes 13 may be formed in the printed circuit board 10, and a coupler 26 corresponding to the through holes 13 may be formed in the bracket 20. The bracket 20 may be mounted on the printed circuit board 10 by a clamping member 40. The clamping member 40 may penetrate the through holes 13 formed in the printed circuit board 10 and may clamp the coupler 26 provided in the bracket 20.

A hole 24 corresponding to a position of the switch 12 of the printed circuit board 10 may be formed in the bracket 20. The hole 24 may be formed on a bottom portion 21 of the bracket 20. When the bracket 20 is mounted on the printed circuit board 10, the switch 12 may be protruded from the bottom portion 21 of the bracket 20 through the hole 24.

The hole 24 may be a little larger than the diameter D2 of the switch 12 so that the switch 12 may be operated in the first direction A or in the second direction B. For example, the hole 24 may be corresponding to a size of the pedestal 11 having a diameter L3 greater than the diameter L4 of the switch 12. The pedestal 11 may be protruded from the bottom portion 21 of the bracket 20 through the hole 24.

An insertion hole 25 into which the rotation axis 33 provided in the operation unit 30 is inserted may be formed on side surface portion 22 of the bracket 20. The rotation axis 33 may be inserted in the insertion hole 25 and rotatable.

The rotation axis 33 is provided on an opposite side of the operation unit 30, and the insertion hole 25 may be formed on two surfaces of the side surface portion 22 opposite each other. A distance L1 between both end portions of the rotation axis 33 may be greater than a distance L2 between two opposite surfaces of the side surface portion 22. The side surface portion 22 of the bracket 20 is movable in the direction of the rotation axis 33 by a predetermined distance, and therefore when the rotation axis 33 is inserted, the side surface portion 22 may be pushed outward by the rotation axis 33 and then restore to the original place when the rotation axis 33 is inserted in the insertion hole 25. Therefore, the operation unit 30 may be installed to be rotatable in the bracket 20.

Support members 23 may be provided in the bottom portion 21 of the bracket 20. When the operation unit 30 is installed in the bracket 20, the support members 23 may support one end portion of the operation unit 30. The support members 23 may be disposed on both sides opposite each other around the hole 24. When the switch 12 operates in the first direction A or in the second direction B, the support members 23 may be disposed at each of positions corresponding to the first direction A and the second direction B around the hole 24.

When the switch 12 operates in various directions such as a third direction, the fourth direction, etc. not shown in the drawing, the support members 23 may be disposed at each of the positions corresponding to operation directions of the switch 12. When the operation direction of the switch 12 is not specified, the support members 23 may be disposed so that one end portion of the switch 12 is entirely supported.

The support members 23 may be formed of elastic materials. For example, the support members 23 may include synthetic resin including rubber, silicon, urethane, etc. The support members 23 may have a dome shape. The support members 23 which support one end portion of the operation unit 30 may be formed of elastic materials, and therefore the operation unit 30 may be restored to a neutral state when the external force applied to the operation unit 30 is removed. Here, the switch 12 fixed to the operation unit 30 may also be restored to a neutral state. The shape of the operation unit 30 is not limited to that described above and may be various shapes.

Figure 7:
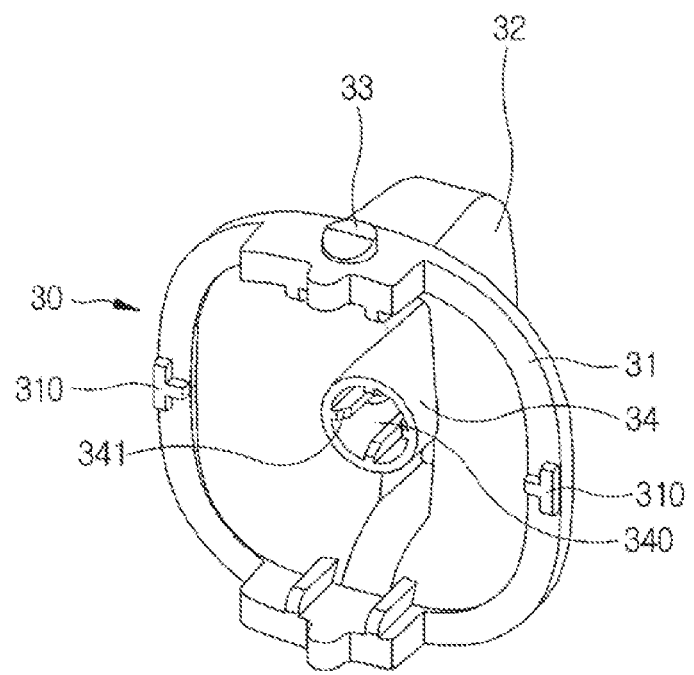
FIG. 7 is a diagram illustrating an operation unit of the switch device according to an exemplary embodiment.
Figure 8:
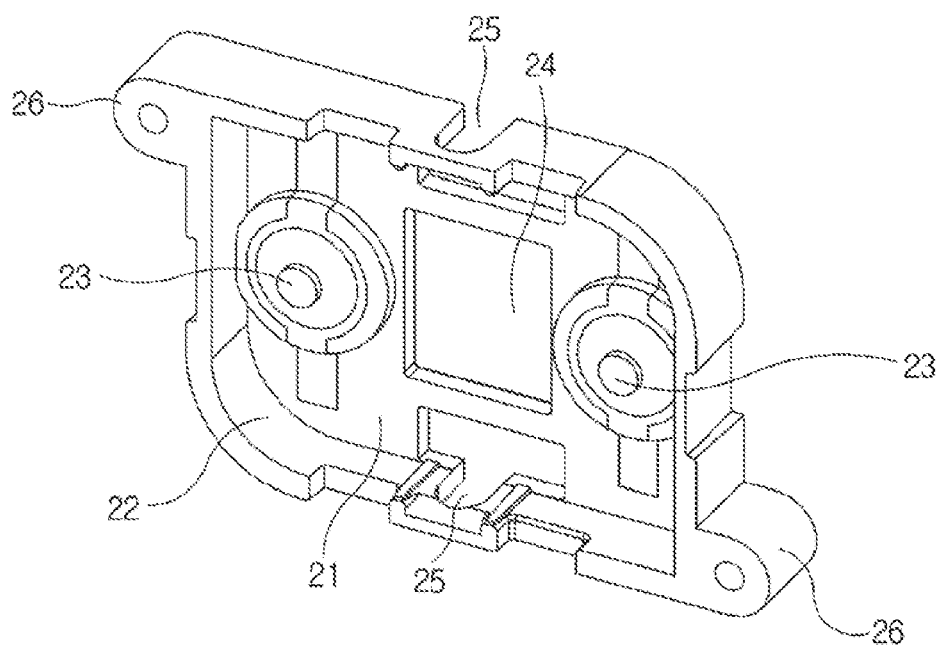
FIG. 8 is a bottom perspective view illustrating a bracket of the switch device according to an exemplary embodiment.
Figure 9:
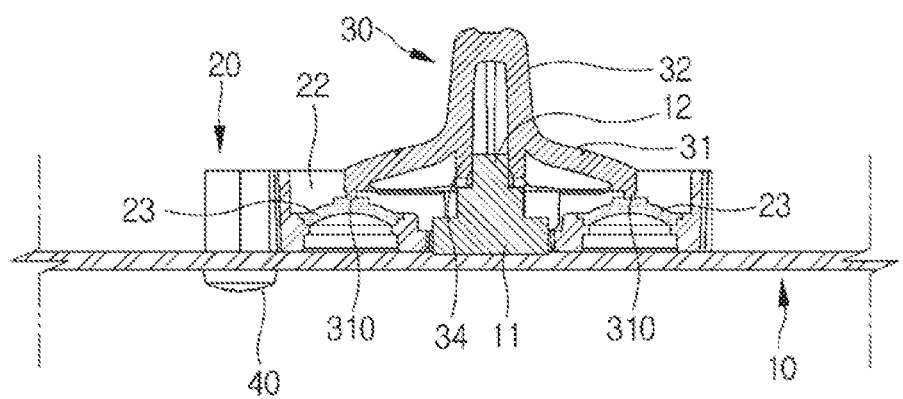
FIG. 9 is a cross-sectional view illustrating the switch device according to an exemplary embodiment.

FIG. 7 is a diagram illustrating an operation unit of the switch device according to an exemplary embodiment, FIG. 8 is a bottom perspective view illustrating a bracket of the switch device according to an exemplary embodiment, and FIG. 9 is a cross-sectional view illustrating the switch device according to an exemplary embodiment.

Referring to FIGS. 7 to 9, the operation unit 30 of the switch device 1 according to an exemplary embodiment may include a body 31, a gripper 32 protruded from the body 31, and a fixing member 34 to which the switch 12 is fixed. The rotation axis 33 may be disposed at one side of the body 31.

When the switch 12 and the operation unit 30 are provided capable of tilting in the first direction A and the second direction B, the rotation axis 33 may be protruded in an axis direction perpendicular to the first direction A and the second direction B.

The rotation axis 33 may be protruded from both sides of the body 31 opposite each other. The rotation axis 33 may be inserted in the insertion hole 25 provided in the bracket 20. The operation unit 30 may rotate about the rotation axis 33 and may be tilted in the first direction A and the second direction B. Because the rotation axis 33 is inserted in the insertion hole 25 provided in the bracket 20, the operation unit 30 may be fixed to the bracket 20 so that the operation unit 30 does not separate from the bracket 20.

The gripper 32 may be protruded from one surface of the body 31. A user may apply an external force to the operation unit 30 through the gripper 32.

The fixing member 34 may be disposed on the other surface of the body 31. The fixing member 34 may be protruded from the other surface of the body 31. The fixing member 34 may include an accommodating member 340 which accommodates at least a part of the switch 12. Fixing ribs 341 fixing the switch 12 may be provided on an inside surface of the fixing member 34 forming the accommodating member 340. A plurality of fixing ribs 341 may be disposed on the inside surface of the fixing member 34 and may be separated from each other by a predetermined distance.

A safe positioning member 310 may be disposed protruding from the other surface of the body 31. When the operation unit 30 is installed in the bracket 20, the safe positioning member 310 may be supported by the support members 23 of the bracket 20. When the switch 12 is tilted in the first direction A and the second direction B, the safe positioning member 310 may be positioned on sides of the first direction A and the second direction B with respect to the extension direction of the rotation axis 33.

The support members 23 including an elastic material may be provided in the bracket 20 of the switch device 1. The bracket 20 may include a synthetic resin material which has strength. The support members 23 may be formed by a double injection molding together with the bracket 20.

The support members 23 may include a material having a suitable elasticity to implement a required restoring force.

An injection molding material or a shape of the support members 23 may be changed according to a magnitude of the restoring force.

The body 31 of the operation unit 30 may cover the hole 24 formed in the bracket 20. The switch 12 may be protruded through the hole 24 provided in the bracket 20, and the protruded switch 12 may be accommodated in the accommodating member 340 provided in the operation unit 30. The switch 12 inserted in the accommodating member 340 may be fixed by the fixing ribs 341 so that the switch 12 may not move in the accommodating member 340.

A user may apply an external force to the operation unit 30 through the gripper 32 provided in the operation unit 30. When the external force is applied to the operation unit 30, the operation unit 30 may rotate about the rotation axis 33 and may be tilted in the first direction A or the second direction B. When the operation unit 30 is tilted, the safe positioning member 310 provided in the operation unit 30 may press the support members 23 of the bracket 20. The shape of the support members 23 may be changed by the safe positioning member 310. The switch 12 may be tilted in the first direction A or the second direction B according to the tilt of the operation unit 30. When the switch 12 is tilted in the first direction A or the second direction B, a signal may be generated so that a specified operation set according to a tilting direction of the switch 12 is performed.

When the external force applied to the operation unit 30 is removed, by the elasticity of the support members 23, the support members 23 may restore to the shape before the support members 23 are changed. As the support members 23 restore to the shape before the support members 23 are changed, the safe positioning member 310 may also restore to a position before being pressurized. Therefore, when the external force applied to the operation unit 30 is removed, the operation unit 30 may be restored to a position before applying the external force.

Conventionally, an operation unit is assembled into a switch by forced insertion, and therefore an operation sensitivity of the switch is not good, and a case where the operation unit becomes separated from the switch may occur. Further, the operation unit installed in the switch may move, therefore lowering the quality of the switch device.

According to an exemplary embodiment, the switch is operated by the rotatable operation unit provided in the bracket, and therefore the operation unit may be fixed not to be separated. The support members including an elastic material may be provided in the bracket so that the displacement of the operation unit may be prevented, and the sensation of using the switch while operating the switch device may be improved.

According to an exemplary embodiment, a switch having degrees of freedom in at least two directions may be easily operated through an operation unit. The restoration of the switch may be improved by fixing the operation unit to the switch with a bracket including a double-injection-molded elastic material.

The switch device according to an exemplary embodiment may be applied to a control panel of medical appliances including an ultrasonic apparatus, an X-ray apparatus, etc., and also to a control panel of various display devices and a control panel of home appliances including a refrigerator, a washing machine, etc. as well as a control panel of an electronic apparatus. The fields in which the switch device according to an exemplary embodiment is applied are not limited to those described above.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An X-ray imaging apparatus comprising:
   an X-ray generator configured to generate X-rays;
   a detector configured to detect X-rays penetrating an object;
   a stand on which the detector is mounted; and
   a control panel mounted on the stand, and configured to operate the detector to rotate or move up or down along an extension direction of the stand, the control panel comprising buttons and a switch device configured to control a movement of the detector,
   wherein the switch device comprises:
   a switch configured to be tiltable on a printed circuit board;
   an operation unit connected to the switch;
   a bracket in which the operation unit is installed to be rotatable; and
   a support member formed of an elastic material, included in the bracket, and provided to support one side of the operation unit.

2. The X-ray imaging apparatus of claim 1, wherein the X-ray generator is configured to move in correspondence to a movement of the detector.

3. The X-ray imaging apparatus of claim 1, wherein the detector is configured to move up when the switch device is pressurized upwards, and to move down when the switch device is pressurized downwards.

4. The X-ray imaging apparatus of claim 1, wherein the detector is configured to move when the switch device is pressurized, and to stop moving when a pressurized state of the switch device is released.

5. The X-ray imaging apparatus of claim 1, wherein the buttons include a shift button, and the X-ray imaging apparatus is configured to perform two or more functions according to whether the shift button is on or off.

6. The X-ray imaging apparatus of claim 1, wherein the support member is formed by a double injection molding.

7. The X-ray imaging apparatus of claim 1, wherein when an external force is applied to the operation unit, the operation unit and the switch are tilted together.

8. The X-ray imaging apparatus of claim 1, wherein when an external force is applied to the operation unit, the support member is pressurized by the operation unit and a shape thereof is changed.

9. The X-ray imaging apparatus of claim 8, wherein when the external force applied to the operation unit is removed, the support member is configured to restore to a shape before the external force is applied.

10. The X-ray imaging apparatus of claim 1, wherein the support member is configured to have a dome shape.

11. The X-ray imaging apparatus of claim 1, further including:
    a safe positioning member which is positioned in the support member and protruded from one side of the operation unit.

12. The X-ray imaging apparatus of claim 1, wherein a hole through which the switch passes is formed on a bottom portion of the bracket.

* * * * *